United States Patent
Berghof

(10) Patent No.: US 10,520,480 B2
(45) Date of Patent: Dec. 31, 2019

(54) DECONVOLUTION METHOD FOR EMISSIONS MEASUREMENT

(71) Applicant: AVL TEST SYSTEMS, INC., Plymouth, MI (US)

(72) Inventor: Frank Berghof, Graz (AT)

(73) Assignee: AVL TEST SYSTEMS, INC., Plymouth, MI (US)

( * ) Notice: Subject to any disclaimer, the term of this patent is extended or adjusted under 35 U.S.C. 154(b) by 0 days.

(21) Appl. No.: 16/036,458

(22) Filed: Jul. 16, 2018

(65) Prior Publication Data

US 2018/0321205 A1 Nov. 8, 2018

Related U.S. Application Data

(63) Continuation of application No. 14/007,111, filed as application No. PCT/US2012/029020 on Mar. 14, 2012, now abandoned.

(60) Provisional application No. 61/468,112, filed on Mar. 28, 2011.

(51) Int. Cl.
*G01N 33/00* (2006.01)
*G01D 3/02* (2006.01)
*G01D 18/00* (2006.01)

(52) U.S. Cl.
CPC ......... *G01N 33/0006* (2013.01); *G01D 3/022* (2013.01); *G01D 18/008* (2013.01)

(58) Field of Classification Search
CPC ... G01N 33/0006; G01D 3/022; G01D 18/008
USPC ........................................................ 702/100
See application file for complete search history.

(56) References Cited

U.S. PATENT DOCUMENTS

| 5,838,598 A | 11/1998 | Hurrell | |
|---|---|---|---|
| 6,271,522 B1 * | 8/2001 | Lindermeir | G01N 21/255 250/338.5 |
| 6,907,383 B2 * | 6/2005 | Eryurek | G01F 1/363 702/100 |
| 7,747,380 B2 | 6/2010 | Chauvin et al. | |
| 2003/0080295 A1 * | 5/2003 | Webber | G01N 21/3504 250/341.2 |

(Continued)

FOREIGN PATENT DOCUMENTS

| AU | 2002227768 B2 | 8/2006 |
|---|---|---|
| JP | 2000039396 A | 2/2000 |

(Continued)

OTHER PUBLICATIONS

Sharma et al., "A Convolution Theorem for the Two Dimensional Fractional Fourier Transform in Generalized Sense," 2010 3rd International Conference on Emerging Trends in Engineering and Technology (ICETET)[online], Nov. 19-21, 2010 [Retrieved on May 22, 2012], pp. 482-484, Retrieved from the Internet: <http://dl.acm.org/citation.cfm?id=1933639>.

(Continued)

*Primary Examiner* — Stephanie E Bloss

(57) ABSTRACT

Disclosed is a method of correcting a response of an instrument. The method includes determining an inverse convolution function, the inverse convolution function being in the time domain. A response of an instrument to an exhaust sample is recorded as a function of time. The recorded response is then convolved with the inverse convolution function, the result being a convolution corrected instrument response.

20 Claims, 5 Drawing Sheets

(56) References Cited

U.S. PATENT DOCUMENTS

| | | | |
|---|---|---|---|
| 2003/0112980 A1* | 6/2003 | Vaishya | G10K 11/178 381/71.1 |
| 2005/0016871 A1* | 1/2005 | Compton | G01N 33/4925 205/782 |
| 2005/0066744 A1* | 3/2005 | Kupnik | G01F 1/662 73/861.03 |
| 2007/0029477 A1* | 2/2007 | Miller | G01N 27/624 250/290 |
| 2008/0006775 A1* | 1/2008 | Arno | G01N 21/05 250/338.5 |
| 2010/0073173 A1* | 3/2010 | Zindy | G01N 15/06 340/627 |
| 2014/0019077 A1 | 1/2014 | Berghof | |

FOREIGN PATENT DOCUMENTS

| | | | |
|---|---|---|---|
| JP | 2000146828 A | 5/2000 | |
| JP | 2001004533 A | 1/2001 | |
| JP | 2003172698 A | 6/2003 | |
| JP | 2003280169 A | 10/2003 | |
| JP | 2004271498 A | 9/2004 | |
| JP | 2010107279 A | 5/2010 | |
| WO | WO-2008008124 A2 | 1/2008 | |
| WO | WO-2010/079377 A1 | 7/2010 | |

OTHER PUBLICATIONS

Albertson et al., "Comparison of different methods to couple nonlinear source descriptions in the time domain to linear system descriptions in the frequency domain—Application to a simple valveless one-cylinder cold engine," Journal of Sound and Vibration [online], Apr. 4, 2006 (Apr. 4, 2006) [Retrieved on May 22, 2012], vol. 291, Iss. 3-5, pp. 963-985, Retrieved from the Internet: <http://www.sciencedirect.com/science/article/pii/S0022460X05004815>.

International Search Report and Written Opinion for PCT/US/2012/029020, dated Jun. 12, 2012, ISA/US.

Pakko, D. James. "Reconstruction of Time-Resolved Vehicle Emissions Measurements by Deconvolution" SAE International. vol. 2, Issue 1. pp. 697-707. (Jan. 2009).

Extended European Search Report for PCT/US2012/029020, dated Feb. 20, 2015.

Japanese Office Action for application No. 2014-502616 dated Dec. 7, 2015.

Chinese Office Action for Application No. 201280020073.6 dated Dec. 3, 2015.

* cited by examiner

DECONVOLUTION METHOD FOR EMISSIONS MEASUREMENT

CROSS-REFERENCE TO RELATED APPLICATIONS

This application is a continuation of U.S. patent application Ser. No. 14/007,111 filed on Sep. 24, 2013, which is a 371 U.S. National Stage of International Application No. PCT/US2012/29020, filed on Mar. 14, 2012, which claims the benefit of U.S. Provisional Application No. 61/468,112, filed on Mar. 28, 2011. The entire disclosures of the applications referenced above are incorporated herein by reference.

BACKGROUND

Emissions analyzers, or measurement instruments, measure certain gaseous constituents within a sample of exhaust, or aerosol, as a function of time, or are configured to measure particulate matter, such as soot, within an exhaust sample, as examples. The response of the instrument, however, may be uncorrected for the convolution of the measurement with some other signal representative of the transfer function, or the transient response, of the instrument. Deconvolution is a process used to reverse, or correct, the effects of convolution.

In one known method, the response of an instrument is recorded online in the time domain. Deconvolution of the recorded signal is performed offline in post-processing by (1) decomposing the recorded data, via a Fourier transform, into the frequency domain, (2) using a model to remove the effects convolution, and then (3) constructing a convolution corrected signal, via an inverse Fourier transform, back into the time domain.

SUMMARY

Disclosed is a method of correcting a response of an instrument. The method includes determining an inverse convolution function, the inverse convolution function being in the time domain. The method further includes recording a response of an instrument to an exhaust sample as a function of time, and convolving the recorded response with the inverse convolution function, the result being a convolution corrected instrument response.

Further disclosed is a method of determining an inverse convolution function. The method includes determining an idealized convolution function, the idealized convolution function being in the time domain. The idealized convolution function is transformed from the time domain to the frequency domain, and a regularizing filter function is divided by the transformed idealized convolution function. The result of the division is the inverse convolution function in the frequency domain. The inverse convolution function is then transformed from the frequency domain to the time domain.

These and other features of the present disclosure can be best understood from the following drawings and detailed description.

BRIEF DESCRIPTION OF DRAWINGS

The drawings can be briefly described as follows.

DETAILED DESCRIPTION

Figure 1:
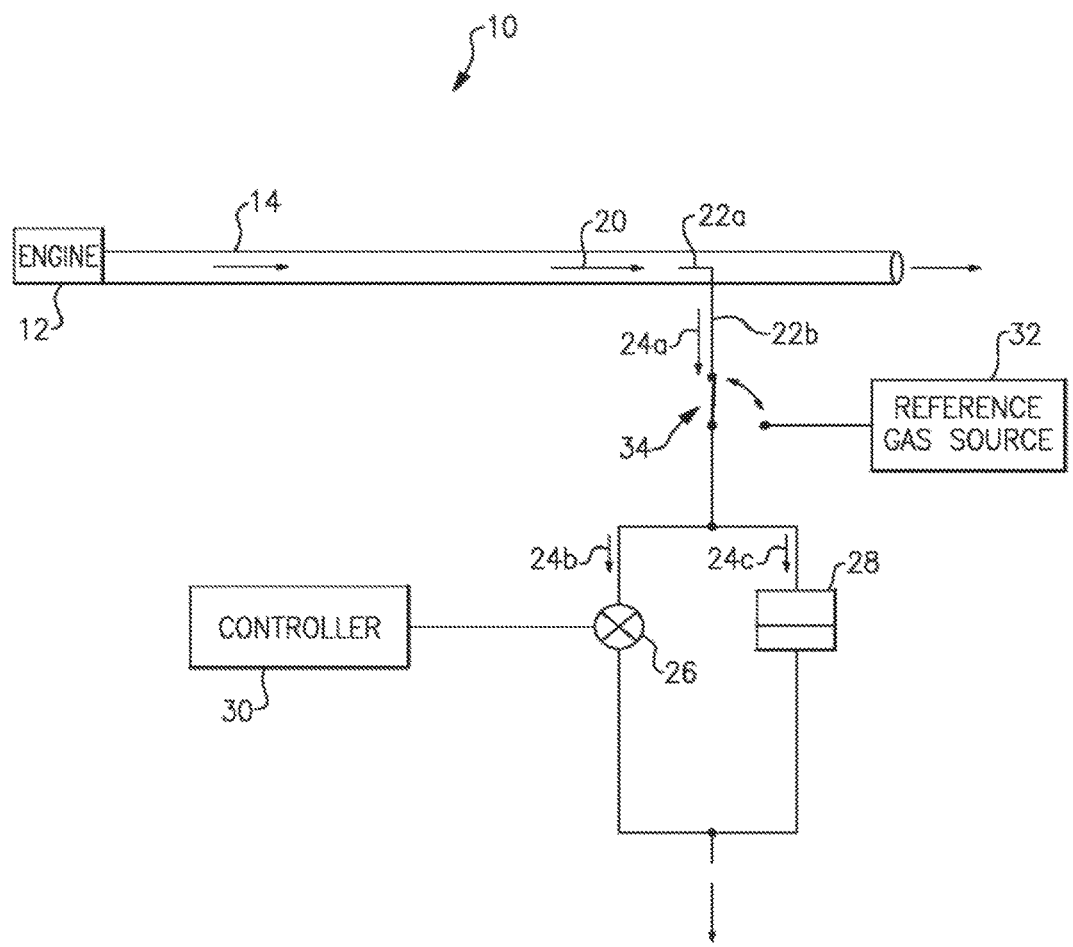
FIG. 1 illustrates an example system including a measurement instrument configured to respond to exhaust.

FIG. 1 illustrates an example system 10 including an engine 12 and an exhaust pipe 14 downstream thereof. The engine 12 could be an engine of a vehicle, or could be a stand-alone engine in a lab, as examples. The engine 12 could further be any type of engine, including a diesel engine.

Exhaust 20 generated from the engine 12 flows downstream of the engine 12, is tapped at 22a, and a sample 24a of the exhaust 20 is directed to a sampling line 22b. A portion 24b of the sample 24a is directed toward a measurement instrument 26, whereas another portion 24c is directed toward a filter box 28 in parallel with the measurement instrument 26. The filter box 28 need not be present, however.

In this example, the measurement instrument 26 is a soot sensor, such as the AVL 483 Micro Soot Sensor (MSS), for example. The response (or, signal) from the measurement instrument 26 is indicative of a concentration of soot, as a function of time, within the portion 24b of the sample 24a.

A controller 30, which may be any type of known computer, is in communication with the measurement instrument 26 to record the response thereof. As those in the art would appreciate, the controller 30 could include a processor (or, CPU), screen, hard drive, mouse, keyboard, etc. The controller 30 is further configured to perform each of the calculations in the steps described below, and may be configured to communicate with other various components in the system 10.

A reference gas source 32 selectively in communication with the sampling line 22b by way of an adjustable valve 34. The controller 30, in one example, is configured to adjust the valve 34, however the valve 34 could be manually adjustable. In this example, the reference gas is a gas having a known soot concentration. The reference gas source 32 can include an appropriate reference gas, however, as will be appreciated from the below.

Notably, while a soot sensor is shown, this disclosure extends to other types of measurement instruments. For example, this disclosure extends to gas analyzers configured to measure a quantity (e.g., a concentration) of one or more gaseous constituents within a sample of exhaust, such as of $CO_2$, $CO$, $NO$, $NO_2$, $NO_x$, $CH_4$, $HC$, $O_2$, $NH_3$, and $N_2O$, as examples. The disclosed method can further be used to deconvolute data from any measurement instrument for which a convolution curve can be determined, such as temperature, pressure, flow rate, speed and torque measurements, as examples. The system 10 is likewise non-limiting, and this disclosure extends to other system set-ups, including those mounted for use on-road or in a lab.

Figure 2:
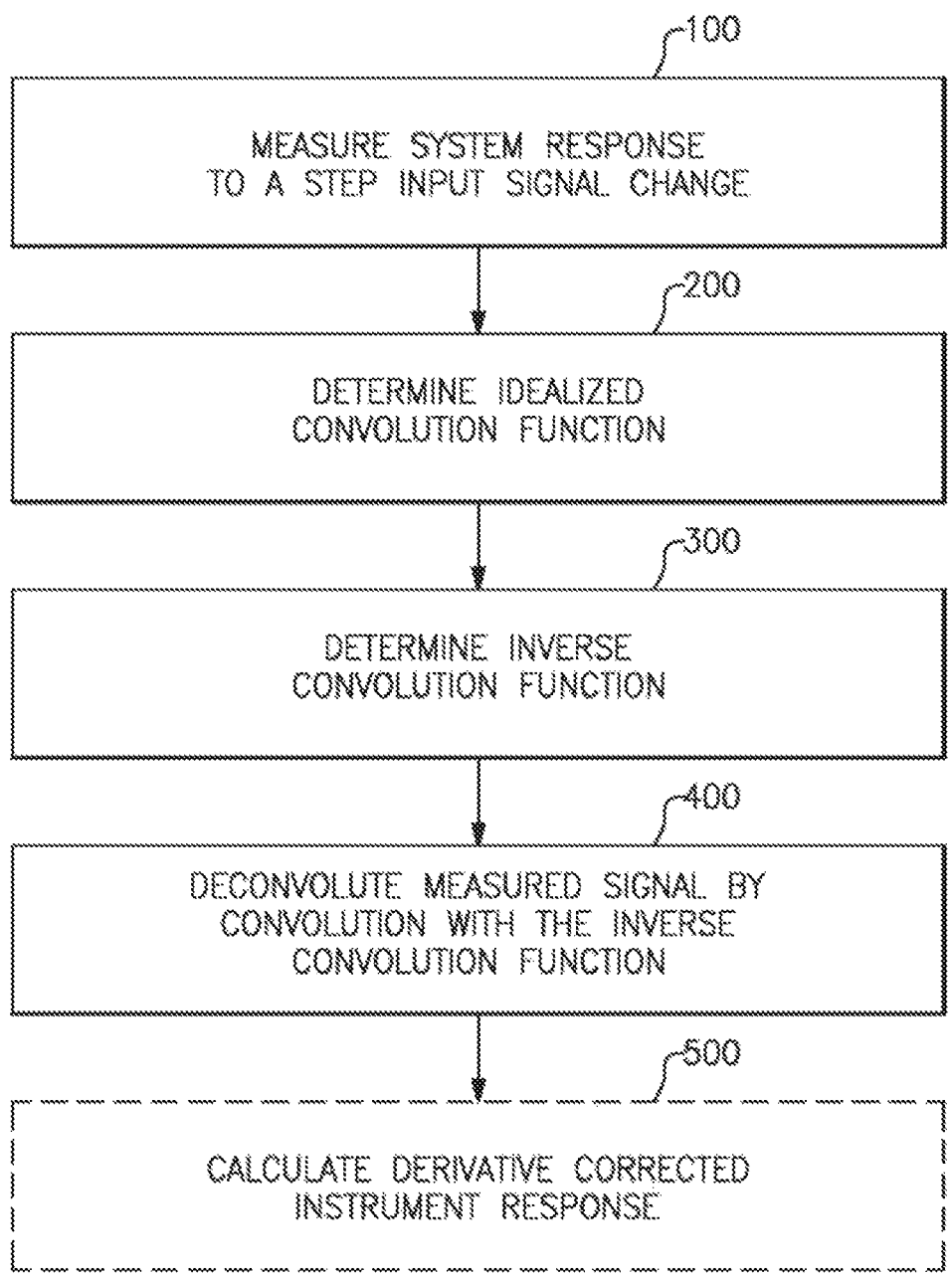
FIG. 2 illustrates an example method of correcting a response of a measurement instrument.

FIG. 2 shows a high-level overview of the steps in one example of the disclosed method. As shown, the response of the system 10 (specifically, the response of the measurement instrument 26) to a step input signal change is measured, at 100. Then, idealized and inverse convolution functions are then determined at 200 and 300, respectively. Steps 100, 200, 300 can be performed offline, before acquiring data during engine operation.

The results from steps 100-300 are then used in the fourth step, at 400, to deconvolute data acquired by the measurement instrument during engine operation. In one example, this data is acquired during an emissions test. The deconvoluted data can be further refined in an optional fifth step, at 500. Steps 100-500 are discussed in detail below.

As those in the art would immediately acknowledge, a function in the time domain is represented as n (t), for example, while the same function in the frequency domain would be represented as N (f). This notation is used throughout the application.

Figure 3:
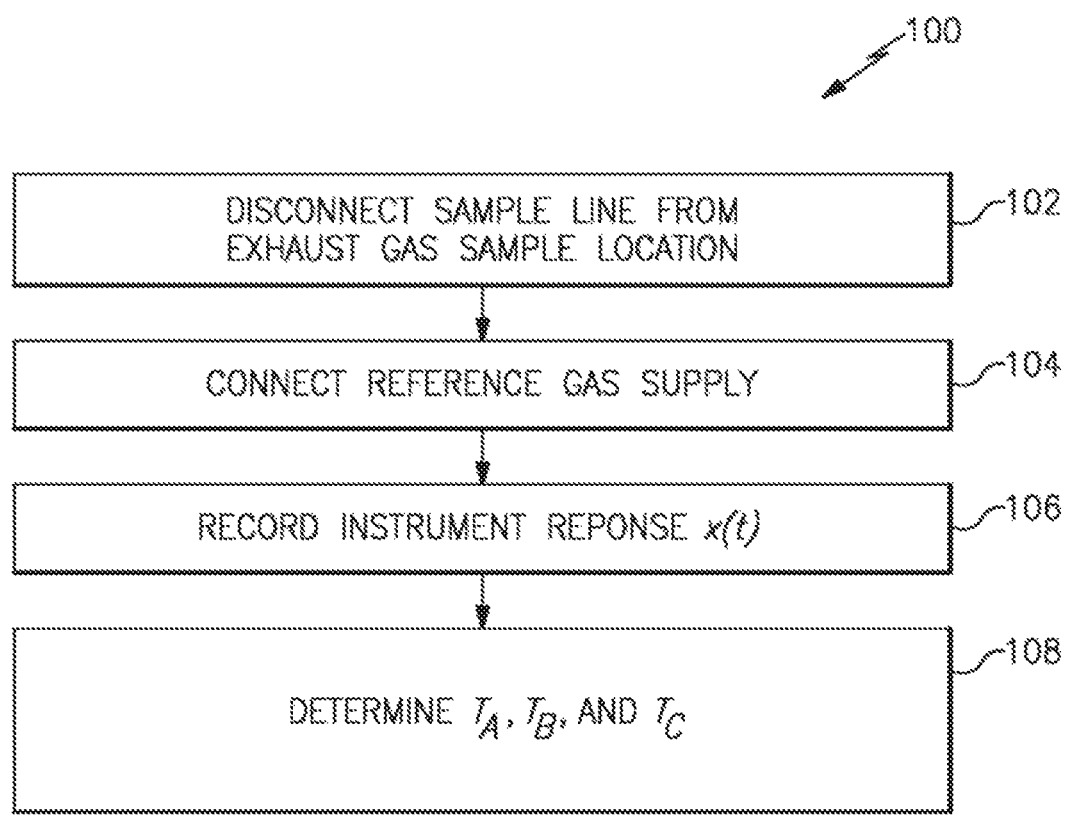
FIG. 3 is representative of the details of the first step from FIG. 2.

FIG. 3 shows the detail of step 100. At 102, 104, and 106, a sample of reference gas, which has a known quantity of a measurable exhaust component, is connected to the measurement instrument, via positioning of the valve 34, and an uncorrected response of the instrument x(t) is recorded. As noted, in the example where the measurement instrument 26 is a soot sensor, the reference gas would have a known soot concentration. Likewise, if the measurement instrument was configured to measure HC, a reference gas with a known HC concentration would be selected.

At 108, times $T_A$, $T_B$, and $T_C$ are determined. As generally noted, these times are times at which the amplitude of the recorded signal is at three different percentage values relative to the known signal. This is indicative of the attenuation caused by the measurement instrument and other measurement equipment. In this example, 10%, 50%, and 90% are used, for $T_A$, $T_B$, and $T_C$, respectively.

Figure 4:
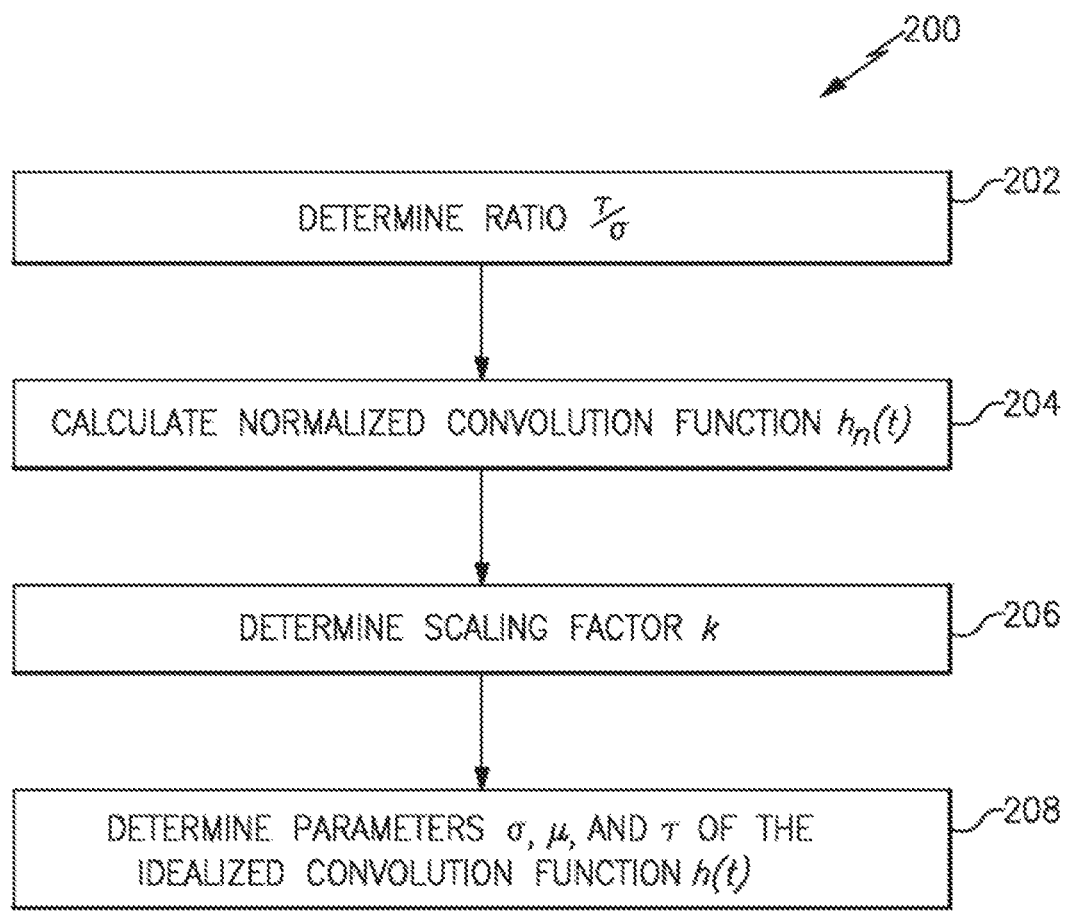
FIG. 4 is representative of the details of the second step from FIG. 2.

FIG. 4 is representative of the details of step 200, the result of which is the determination of h(t), the idealized convolution function. This function generally represents an approximation of the real convolution function, using a model consisting of the Gauss function convoluted with the impulse response function:

$$h(t)=g(t)*i(t)$$

where g(t) is the Gaussian function is defined as:

$$\frac{1}{\sigma\sqrt{2\pi}}e^{-\left(\frac{(t-\mu)^2}{2\sigma^2}\right)}$$

and where i(t) is the impulse response function, defined as:

$$\frac{1}{\tau}e^{-\left(\frac{t}{\tau}\right)}, \text{ for } t \geq 0.$$

At step 202 the ratio $$\frac{\tau}{\sigma}$$

is determined, which is needed to calculate the normalized convolution function $h_n(t)$ in step 204. In one example the ratio $$\frac{\tau}{\sigma}$$

is determined from the following equation:

$$\frac{T_B - T_A}{T_C - T_A}.$$

In another example, a look-up table is used to determine the ratio. The inputs to an example look-up table are $T_A$, $T_B$, and $T_C$.

At step 204 the normalized convolution function $h_n(t)$ is calculated. The normalized convolution function is:

$$h_n(t)=g_n(t)*i_n(t)$$

where $g_n(t)$ is the Gaussian function g(t) from above, with $\mu=0$ and $\sigma=1$:

$$\frac{1}{\sqrt{2\pi}}e^{-\left(\frac{t^2}{2}\right)}$$

and where $i_n(t)$ is the impulse response function i(t) from above, with $\tau_n$ equal to the ratio $$\frac{\tau}{\sigma}$$

determined in step 202:

$$\frac{1}{\tau_n}e^{-\left(\frac{t}{\tau_n}\right)}, \text{ for } t \geq 0$$

A scaling factor k is determined at step 206, and is defined as:

$$k = \frac{T_C - T_A}{T_{C,n} - T_{A,n}}$$

where $T_{A,n}$ is the time at which $\int h_n(t)$ reaches A % of its maximum value (in this example, 10%), and where $T_{C,n}$ is the time at which $\int h_n(t)$ reaches C % of its maximum value (in this example 90%).

At 208, scaling factor k can be used to determine the parameters σ, μ, and τ of the idealized convolution function h(t) based on the following equations:

$$\sigma=k$$

$$\mu=kT_{B,n}$$

$$\tau=k\tau_n$$

where $T_{B,n}$ is the time at which $\int h_n(t)$ reaches B % of its maximum value (in this example, 50%). Having solved for these parameters, the idealized convolution function h(t) can then be determined by solving for g(t) and i(t), above.

As an alternative to step 200, the idealized convolution function h(t) could be approximated as the first derivative of the uncorrected instrument response x(t).

Figure 5:
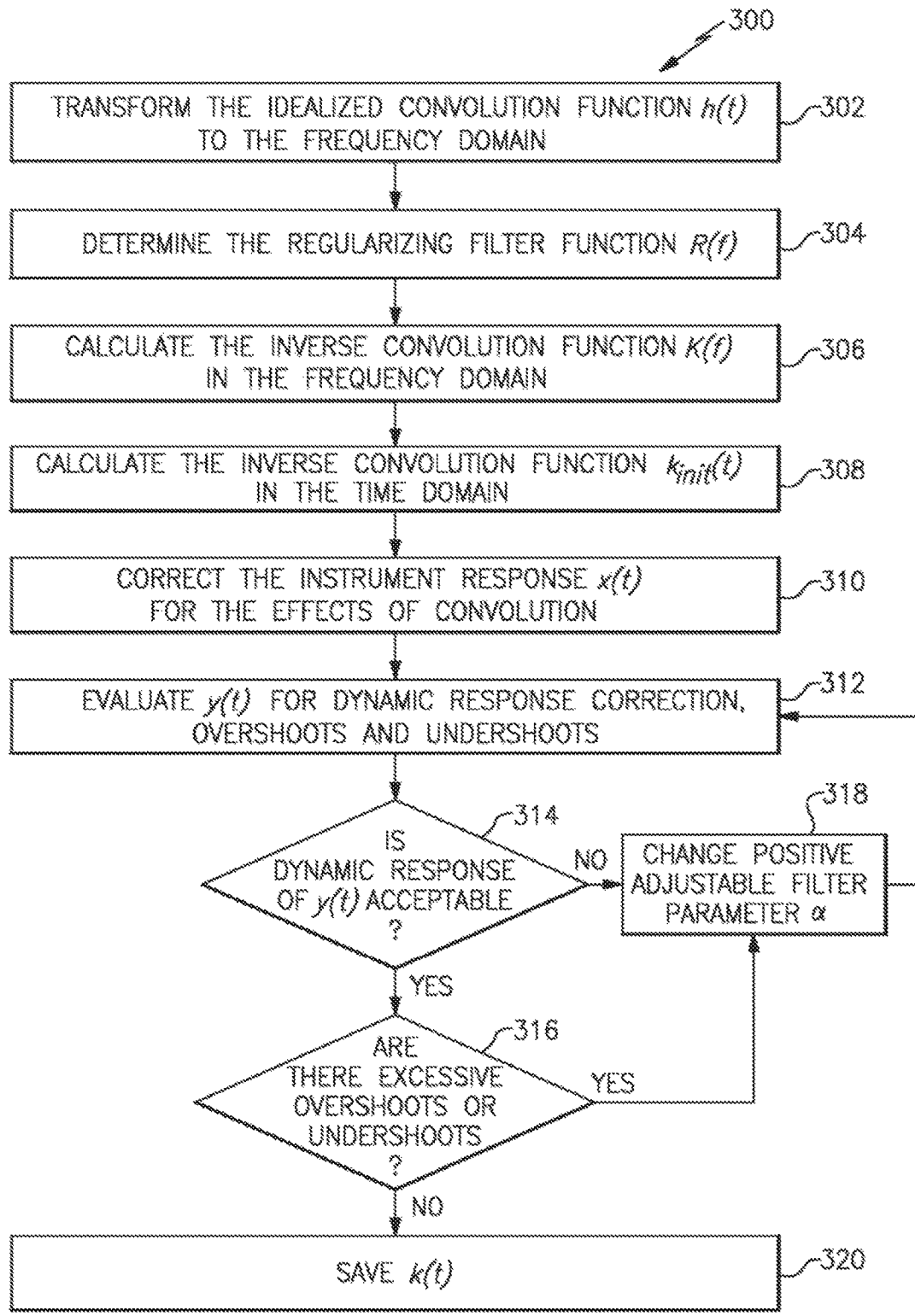
FIG. 5 is representative of the details of the third step from FIG. 2.

FIG. 5 generally illustrates the steps for determining the inverse convolution function k(t). At 302, the idealized convolution function h(t) is transformed into the frequency domain by Fourier transformation, as follows:

$$H(f)=F(h(t))$$

Next, as 304, a regularizing filter function R(f) is calculated from the following equation:

$$R(f) = \frac{(H_{MAG}(f))^2}{(H_{MAG}(f))^2 + \alpha}$$

where $H_{MAG}(f)$ is the magnitude, or absolute value, of H(f), and where α is a positive adjustable filter parameter. In one example, α is a constant, positive real value. In another example, α is a function of frequency, however a constant value is typically sufficient. As noted below, in the example where α is a constant, α can be tuned to adjust the convolution corrected instrument response y(t).

At 306 the inverse convolution function K(f) is calculated by:

$$K(f) = R(f)/H(f)$$

Notably, R(f) and H(f) may include complex numbers, and thus, in one example, the above division follows the rules for division of two complex numbers and can be performed by dividing the magnitude of R(f) (e.g., $R_{MAG}(f)$) by the magnitude of H(f) (e.g., $H_{MAG}(f)$) and subtracting the phase angle of H(f) (e.g., $H_{PHA}(f)$) from the phase angle of R(f) (e.g., $R_{PHA}(f)$).

At 308, the inverse convolution function K(f) is converted into the time domain by way of an inverse Fourier transformation to determine an initial inverse convolution function $k_{init}(t)$:

$$k_{init}(f) = F^{-1}(K(f)).$$

The regularizing filter function R(f) depends from a positive adjustable filter parameter α, which may be a constant value, and need not be frequency dependent. The positive adjustable filter parameter α is generally representative of a signal to noise ratio.

Once $k_{init}(t)$ is determined, the uncorrected instrument response x(t) recorded in step 100 is convolved with $k_{init}(t)$ to construct an convolution corrected instrument response y(t), at step 310, as follows:

$$y(t) = x(t) * k_{init}(t)$$

The convolution corrected instrument response y(t) can then be evaluated relative to the known reference gas signal from step 100, at step 312. In one example this evaluation is performed by graphically comparing the two signals, however this could also be performed using a one-dimensional optimization algorithm to minimize the sum of squares of the deviations between the deconvoluted response and the signal representative of the known data.

As represented in steps 314, 316, and 318, the positive adjustable filter parameter α can further be adjusted, or "tuned," to increase the accuracy of the inverse convolution function $k_{init}(t)$, thus increasing the accuracy of the convolution corrected instrument response y(t) relative to the reference gas signal from step 100.

Tuning is dependent on varying the constant positive adjustable filter parameter α, from which $k_{init}(t)$ depends. The dynamic response (or, slope) of y(t) is assessed at 314, while overshoots and undershoots (e.g., amplitude) of y(t) are accounted for at 316. As an example, increasing a would reduce the slope of y(t) (e.g., worse recovery of dynamic response) but also lower the over and undershoots. Once a desirable α is found (e.g., a value for α representing an acceptable compromise between error in slope and error due to over/undershoots is determined), the corresponding inverse convolution function is saved as k(t), at 320, for later use in step 400.

Referring again to FIG. 2, in step 400, the k(t) saved at 320 is used for deconvolution of the uncorrected instrument response m(t). In step 400, the system 10 would be arranged as shown in FIG. 1, for example, such that valve 34 is adjusted so that the sample 24a sourced from the engine 12 is directed toward the instrument 26.

To construct the convolution corrected instrument response y(t), the uncorrected instrument response m(t) is convolved with k(t):

$$y(t) = m(t) * k(t)$$

In one example, the controller 30 executes the convolution of m(t) with k(t) by way of the following Riemann sum:

$$y_i = \sum_{j=1}^{n} k'_j m_{i-(j-1)}$$

where $y_i$ is the i-th value of the convolution corrected instrument response vector, $m_{i-(j-1)}$ is the i–(j–1)-th value of the uncorrected measured instrument response vector, k' is the flipped inverse convolution function in the time domain (as used herein, "flipped" means that the order of the values in the vector is reversed), n is the number of values in the inverse convolution function vector, j is the running index of the inverse convolution function vector, and i is the running index of the uncorrected instrument response vector.

Since the convolution corrected instrument response y(t) is calculated, at 400, entirely in the time domain using multiplication and summation, the calculation at step 400 can be done quickly and efficiently relative to other methods, such methods require transformations between the time and frequency domains. Post processing is thus not necessary with this disclosed method, and the convolution corrected instrument response y(t) can be determined online, during engine operation. Again, as noted above, the controller 30 can be used calculate the convolution corrected instrument response y(t).

At optional step 500, the convolution corrected instrument response y(t) can be further refined to eliminate deviations that may be present at step changes. In one example, this further refinement, called a derivative corrected instrument response p(t), can be calculated by solving for p(t) using the following equation:

$$p(t) + \beta \left(\frac{dp}{dt}\right) * k(t) = y(t)$$

where β is a constant, k(t) is the inverse convolution function from 320, and y(t) is the convolution corrected instrument resulting from 400. In one example, p(t) is solved for iteratively, using y(t) as an initial estimate for p(t). Again, this fifth step is optional, and need not be included.

Although the different examples have the specific components shown in the illustrations, embodiments of this invention are not limited to those particular combinations. It is possible to use some of the components or features from one of the examples in combination with features or components from another one of the examples.

One of ordinary skill in this art would understand that the above-described embodiments are exemplary and non-lim-

The invention claimed is:

1. A system comprising:
an emissions measurement instrument configured to:
measure a concentration of an emission in a sample of exhaust gas from an engine; and
generate an uncorrected instrument response indicating the measured emission concentration as a function of time;
memory configured to:
record the uncorrected instrument response; and
store an inverse convolution function, wherein the inverse convolution function is in the time domain and represents an inverse of the transient response of the emissions measurement instrument; and
a processor configured to:
retrieve the uncorrected instrument response and the inverse convolution function from the memory;
convolve the uncorrected instrument response with the inverse convolution function to mitigate the effect of the transient response of the emissions measurement instrument on the uncorrected instrument response, the result of the convolution being a convolution corrected instrument response; and
output a signal indicating the convolution corrected instrument response.

2. The system of claim 1, wherein the processor is configured to determine the inverse convolution function based on an idealized convolution function, the idealized convolution function being in the time domain.

3. The system of claim 2, wherein the idealized convolution function is the first derivative of a response of the emissions measurement instrument to a reference gas sample.

4. The system of claim 2, wherein the processor is configured to calculate the idealized convolution function by convolving a Gaussian function with an impulse response function.

5. The system of claim 4, wherein the processor is configured to:
determine a scaling factor based on a normalized convolution function and a response of the emissions measurement instrument to a reference gas sample; and
determine the Gaussian and impulse response functions based on the scaling factor.

6. The system of claim 5, wherein the processor is configured to calculate the normalized convolution function by convolving a normalized Gaussian function with a normalized impulse response function.

7. The system of claim 6, wherein the processor is configured to determine the impulse response function based on values from the response of the emissions measurement instrument to the reference gas sample.

8. The system of claim 2, wherein the processor is configured to:
transform the idealized convolution function from the time domain to the frequency domain;
determine the inverse convolution function based on the idealized convolution function, the inverse convolution function initially being in the frequency domain; and
transform the idealized convolution function from the frequency domain to the time domain.

9. The system of claim 8, wherein the processor is configured to divide a regularizing filter function by the transformed idealized convolution function, the result of the division being the inverse convolution function in the frequency domain.

10. The system of claim 9, wherein the processor is configured to determine the regularizing filter function based on the transformed idealized convolution function and a positive adjustable filter parameter.

11. The system of claim 10, wherein the positive adjustable filter parameter is a constant value independent of frequency.

12. The system of claim 10, wherein the processor is configured to adjust the positive adjustable filter parameter to adjust overshoots, undershoots, and a dynamic response of the inverse convolution function.

13. The system of claim 1, wherein the processor is configured calculate a derivative corrected instrument response to eliminate noise at step changes in the convolution corrected instrument response.

14. The system of claim 1, wherein the processor is configured to calculate a derivative corrected instrument response by solving for p(t) using the following equation:

$$p(t) + \beta \frac{dp}{dt} k(t) = y(t),$$

where p(t) is the derivative corrected instrument response, β is a constant, k(t) is the inverse convolution function, and y(t) is the convolution corrected instrument response.

15. The system of claim 1 further comprising:
a sample line configured to deliver the exhaust gas sample to the emissions measurement instrument; and
a valve disposed in the sample line and adjustable between a first position and a second position, wherein valve allows a reference gas sample to flow to the emissions measurement instrument when the valve is in the first position, and the valve allows the exhaust gas sample to flow to the emissions measurement instrument when the valve is in the second position.

16. The system of claim 15, wherein the processor is configured to:
determine the inverse convolution function based on a response of the emissions measurement instrument to the reference gas sample;
adjust the valve to the first position when determining the inverse convolution function; and
adjust the valve to the second position when correcting the response of the emissions measurement instrument to the exhaust gas sample.

17. A system comprising:
an emissions measurement instrument configured to measure a concentration of an emission in a reference gas sample;
memory configured to:
record a response of the emissions measurement instrument to the reference gas sample as a function of time; and
store an idealized convolution function, the idealized convolution function being in the time domain and representing the transient response of an the emissions measurement instrument; and
a processor configured to:
retrieve the idealized convolution function from the memory;

transform the idealized convolution function from the time domain to the frequency domain;

divide a regularizing filter function by the transformed idealized convolution function, the result of the division being an inverse convolution function in the frequency domain;

transform the inverse convolution function from the frequency domain to the time domain using the processor;

output a signal indicating the inverse convolution function in the time domain, wherein the memory is configured to store the inverse convolution function in the time domain;

convolve the recorded response with the transformed inverse convolution function to mitigate the effect of the transient response of the emissions measurement instrument on the recorded response, the result of the convolution being a convolution corrected instrument response indicating the measured emission concentration; and generate a signal indicating the convolution corrected instrument response.

18. The system of claim 17, wherein the processor is configured to calculate the idealized convolution function by convolving a Gaussian function with an impulse response function.

19. The system of claim 17, wherein the processor is configured to:

compare the convolution corrected instrument response signal to a reference gas signal indicating a predetermined concentration of the emission in the reference gas sample;

adjust the inverse convolution function based on the comparison; and output a signal indicating the inverse convolution function as adjusted.

20. The system of claim 19, wherein the processor is configured to:

determine the regularizing filter function based on the transformed idealized convolution function and a positive adjustable filter parameter, wherein the positive adjustable filter parameter is a constant value independent of frequency; and adjust the positive adjustable filter parameter to adjust overshoots, undershoots, and a dynamic response of the convolution corrected instrument response relative to the reference gas signal.

* * * * *